United States Patent
Isayama et al.

(10) Patent No.: US 12,390,623 B2
(45) Date of Patent: Aug. 19, 2025

(54) METHOD FOR FORMING ACCESS ROUTE TO BILE DUCT

(71) Applicants: Hiroyuki Isayama, Hachioji (JP); OLYMPUS MEDICAL SYSTEMS CORP., Hachioji (JP)

(72) Inventors: Hiroyuki Isayama, Tokyo (JP); Tomohiko Mamiya, Kawasaki (JP); Yutaka Yanuma, Tokyo (JP)

(73) Assignees: Hiroyuki Isayama, Tokyo (JP); OLYMPUS MEDICAL SYSTEMS CORP., Tokyo (JP)

( * ) Notice: Subject to any disclaimer, the term of this patent is extended or adjusted under 35 U.S.C. 154(b) by 731 days.

(21) Appl. No.: 17/682,517

(22) Filed: Feb. 28, 2022

(65) Prior Publication Data

US 2022/0176089 A1    Jun. 9, 2022

Related U.S. Application Data

(63) Continuation-in-part of application No. 17/081,270, filed on Oct. 27, 2020, now Pat. No. 11,633,209.

(51) Int. Cl.
| | |
|---|---|
| A61B 17/34 | (2006.01) |
| A61F 2/04 | (2013.01) |
| A61M 27/00 | (2006.01) |
| A61M 29/02 | (2006.01) |
| A61B 17/32 | (2006.01) |
| A61M 25/09 | (2006.01) |

(52) U.S. Cl.
CPC ....... *A61M 27/002* (2013.01); *A61B 17/3478* (2013.01); *A61F 2/04* (2013.01); *A61M 29/02* (2013.01); *A61B 2017/320056* (2013.01); *A61F 2002/041* (2013.01); *A61M 25/09* (2013.01)

(58) Field of Classification Search
CPC ............ A61B 17/3403; A61B 17/3413; A61B 17/3423; A61B 17/3478; A61B 17/3496
See application file for complete search history.

(56) References Cited

U.S. PATENT DOCUMENTS

| | | | |
|---|---|---|---|
| 2009/0069822 A1* | 3/2009 | Takahashi | ............ A61B 17/068 606/139 |
| 2009/0318831 A1 | 12/2009 | Aoki et al. | |
| 2013/0325038 A1 | 12/2013 | Sato | |
| 2018/0280669 A1 | 10/2018 | Shlomovitz et al. | |

FOREIGN PATENT DOCUMENTS

| | | |
|---|---|---|
| JP | 2013-507185 A | 3/2013 |
| WO | 2011-044192 A1 | 4/2011 |

OTHER PUBLICATIONS

Dec. 30, 2022 Notice of Allowance issued in U.S. Appl. No. 17/081,270.

* cited by examiner

*Primary Examiner* — Nicholas W Woodall
(74) *Attorney, Agent, or Firm* — Oliff PLC

(57) ABSTRACT

A method of forming an access route to the bile duct includes: forming a tunnel extending from an oral ridge of a duodenal papilla, which is located on an oral side of a natural opening of a duodenal papilla, to the bile duct; and dilating a lumen of the tunnel more than when it was formed.

20 Claims, 16 Drawing Sheets

METHOD FOR FORMING ACCESS ROUTE TO BILE DUCT

BACKGROUND

Technical Field

The present invention relates to a method for forming an access route to the bile duct, and more specifically, a method for forming the access route to the bile duct from within the duodenum without touching an opening of the duodenal papilla. A treatment method using the method for forming the access route is also provided.

Background Art

Endoscopic retrograde cholangiopancreatography (ERCP) remains a challenging procedure. Post-ERCP pancreatitis is a frequent complication and can be severe or fatal.

It is thought that post-ERCP pancreatitis is developed as a result of impaired outflow of pancreatic fluid (obstruction of pancreatic duct opening) by papilledema and papilledema sphincter spasm, which is caused when a natural opening of a duodenal papilla, a common duct after a bile duct and a pancreatic duct merge, and an ostium of the pancreatic duct, which is a confluence of the pancreatic duct and the bile duct, or the like is stimulated when accessing the bile duct. Therefore, access to the bile duct without touching the ostium of the pancreatic duct, the opening of the duodenal papilla, and the common duct may suppress post-ERCP pancreatitis.

Published Japanese Translation No. 2013-507185 of the PCT International Publication discloses a technique in which a needle is inserted into the duodenum and the common bile duct from within the duodenum, and a stent is placed in the formed tunnel. The stent is placed so that it is exposed in the abdominal cavity, and a route is formed through which bile is drained from the common bile duct without passing through the duodenal papilla.

SUMMARY

A method for forming an access route to the bile duct according to an aspect of the present invention includes: forming a tunnel extending from an oral ridge of the duodenal papilla, which is located on an oral side of a natural opening of the duodenal papilla, to the bile duct; and dilating a lumen of the tunnel more than when it was formed.

A method for forming an access route to a bile duct according to another aspect of the present invention includes: forming a tunnel extending from an oral ridge of a duodenal papilla, which is located on an oral side of a natural opening of a duodenal papilla, to the bile duct; and placing a stent in the tunnel.

A method for forming an access route to a bile duct according to another aspect of the present invention includes: forming a tunnel extending from an oral ridge of a duodenal papilla, which is located on an oral side of a natural opening of a duodenal papilla, to the bile duct, wherein the tunnel is formed by piercing a needle, which is configured to energize a tissue, from the oral ridge toward the bile duct.

DETAILED DESCRIPTION OF THE PREFERRED EMBODIMENTS

An embodiment of the present invention will be described with reference to FIGS. 1 to 14.

First, a flexible endoscope having a flexible insertion portion is inserted into the luminal organ through the patient's mouth or nose, and the distal end portion is moved to the vicinity of the duodenal papilla.

Figure 1:
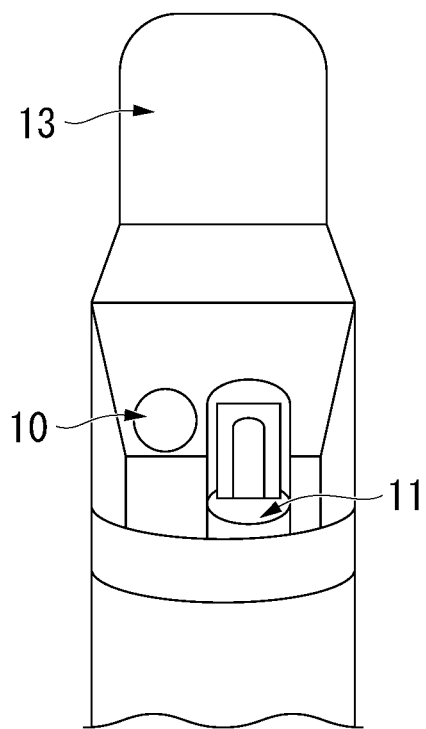
FIG. 1 is a diagram showing an example of an endoscope used in an access route-forming method of the present invention.
Figure 2:
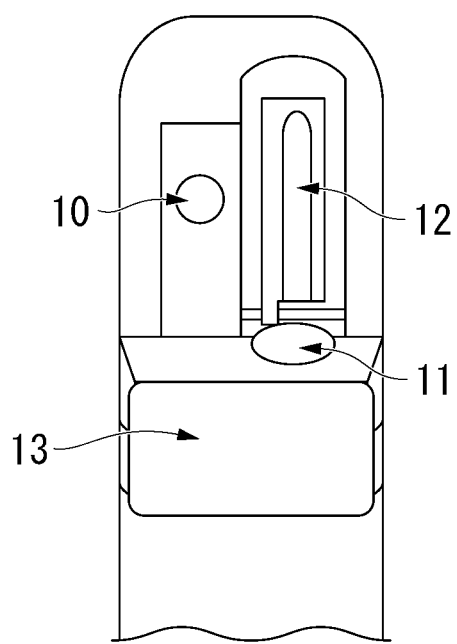
FIG. 2 is a diagram showing another example of the endoscope.

The endoscope used in the present embodiment is a duodenal endoscope that includes an optical observation part 10 and an ultrasound vibrator 13 and is capable of optical observation and ultrasound observation. There are two types of such endoscope. FIG. 1 shows a first type, in which the ultrasound vibrator 13 is located forward of an outlet 11 of the treatment device channel. FIG. 2 shows a second type, in which the ultrasound vibrator 13 is located more proximally than the outlet 11 of the treatment device channel. Both the first type and the second type can be used for the method for forming an access route to the bile duct according to the present embodiment (hereinafter, simply referred to as "route-forming method").

Figure 3:
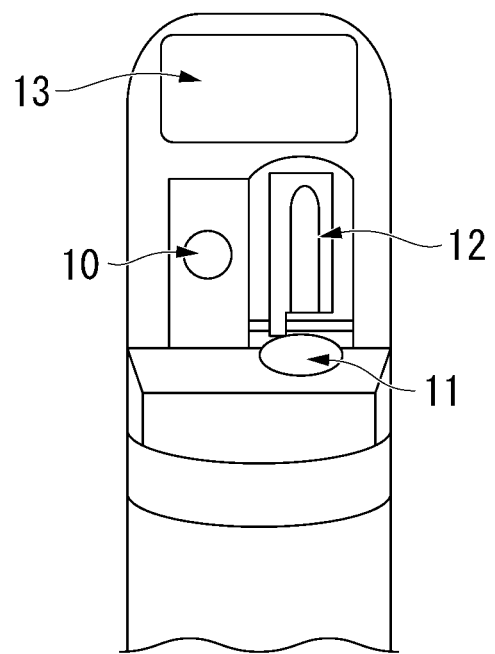
FIG. 3 is a diagram showing another example of the endoscope.

In an endoscope, it is desirable that the visual field direction of the optical observation part 10 be 90° or more in the distal end direction relative to the endoscope axis (longitudinal axis of the elongated insertion portion)(the visual field direction of the optical observation part 10 is directed proximally in the endoscope axis). In addition, it is desirable to have a forceps-raising base that directs the treatment device 90° or more in the distal end direction relative to the endoscope axis (directs the treatment device proximally in the endoscope axis). In the endoscope shown in FIG. 2, the visual field direction of the optical observation part 10 is 90° or more in the distal end direction relative to the endoscope axis (the visual field direction of the optical observation part 10 is directed proximally in the endoscope axis), and a raising base 12 allows the treatment device coming out of the outlet 11 to be directed 90° or more in the distal end direction relative to the endoscope axis (directed proximally in the endoscope axis). The endoscope shown in FIG. 3 is of the first type, but the arrangement and orientation of the optical observation part 10 are different from those of the endoscope shown in FIG. 1, and the visual field direction of the optical observation part 10 is directed 90° or more in the distal end direction relative to the endoscope axis (directed proximally in the endoscope axis). Further, the raising base 12 can direct the treatment device coming out of the outlet 11 to 90° or more in the distal end direction relative to the endoscope axis (directed proximally in the endoscope axis).

Next, the duodenal papilla is imaged in the field of view of the optical observation part 10 of the endoscope. This operation is the same as the operation in a general ERCP or the like, and is performed by appropriately combining an advance/retract operation, a bending operation, a twisting operation, and the like of the endoscope. When imaging the duodenal papilla in the field of view, it is desirable to position the duodenal papilla in front (center) of the optical image.

Next, water is supplied into the duodenum, and water is stored in the duodenum where the distal end of the endoscope is located.

Water can be supplied by using a water supply function of the endoscope, a syringe passed through the treatment device channel of the endoscope, or the like.

Figure 4:
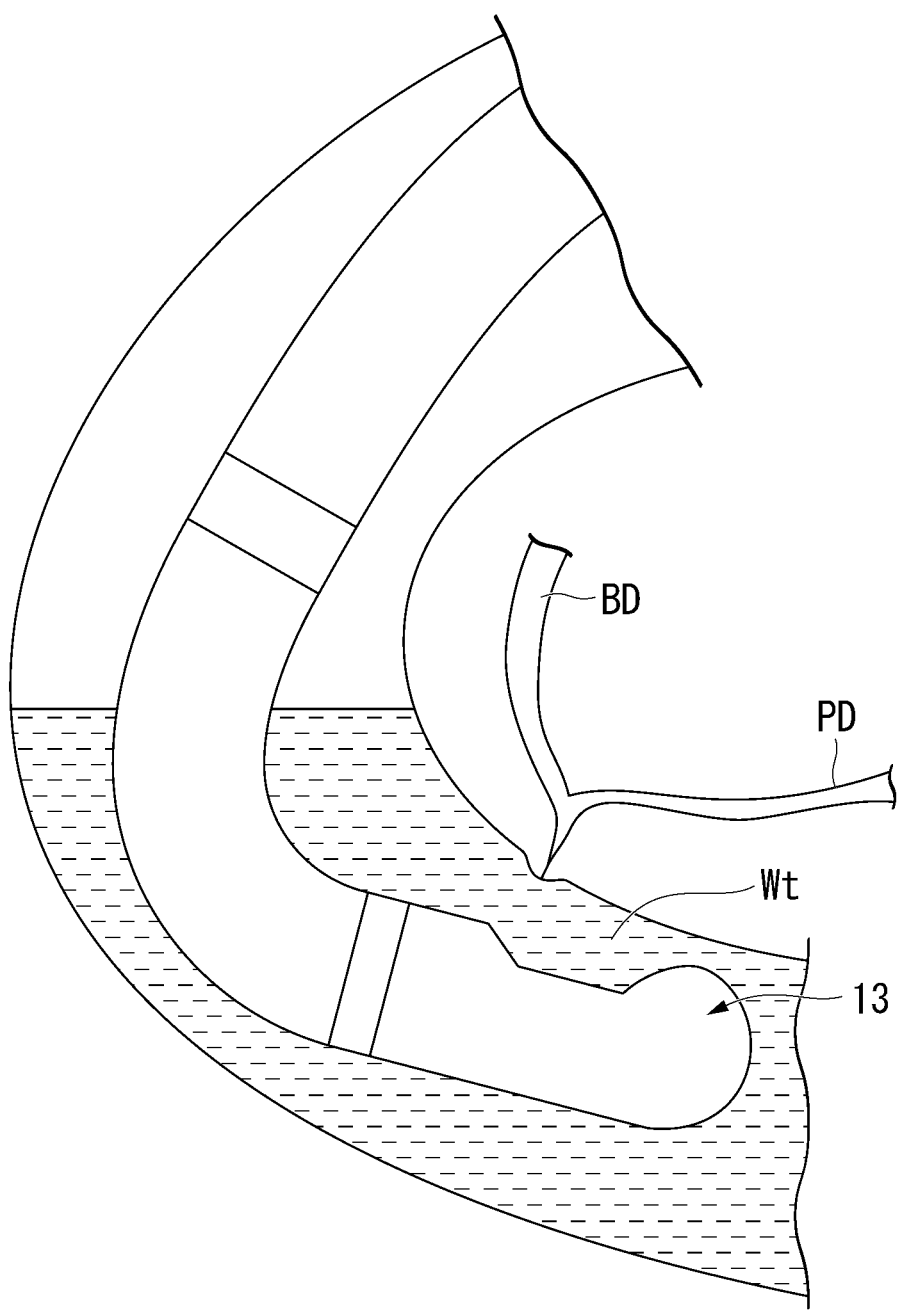
FIG. 4 is a diagram showing one process of the access route-forming method according to an embodiment of the present invention.

As shown in FIG. 4, water is stored to such an extent that the space between the ultrasound vibrator 13 and the duodenal wall and the space between the endoscopic treatment device channel outlet and the duodenal wall are filled with water Wt. As a result, an environment is created in which the bile duct BD, the pancreatic duct PD, and the sheath and needle (described later) protruding from the treatment device channel can be imaged in an ultrasound endoscopic image using the ultrasound vibrator 13.

The posture of the patient when storing water in the duodenal area is preferably the prone position or the left lateral decubitus position, and may be the supine position. The prone position is a common posture in ERCP and can be easily performed.

Balloons may be used to store water, if desired. It is possible to prevent water from moving to the stomach side by introducing the endoscope into the duodenum with the endoscope passed through an overtube with a balloon attached to the outer circumference and inflating the balloon in the duodenum closer to the mouth than the duodenal papilla.

After storing the water, the operator operates the ultrasound vibrator 13 to acquire an ultrasound image, and confirms that the bile duct and pancreatic duct can be imaged. The water to be stored may be degassed water or may contain an electrolyte or the like such as a physiological saline solution.

Once the environment for imaging the ultrasound image is ready, the operator confirms whether the bile duct/the pancreatic duct is imaged in the ultrasound image before the insertion position is aligned on the optical image.

Next, the operator inserts the puncture device into the treatment device channel from the entrance of the treatment device channel provided in the operation part of the endoscope.

Figure 5:
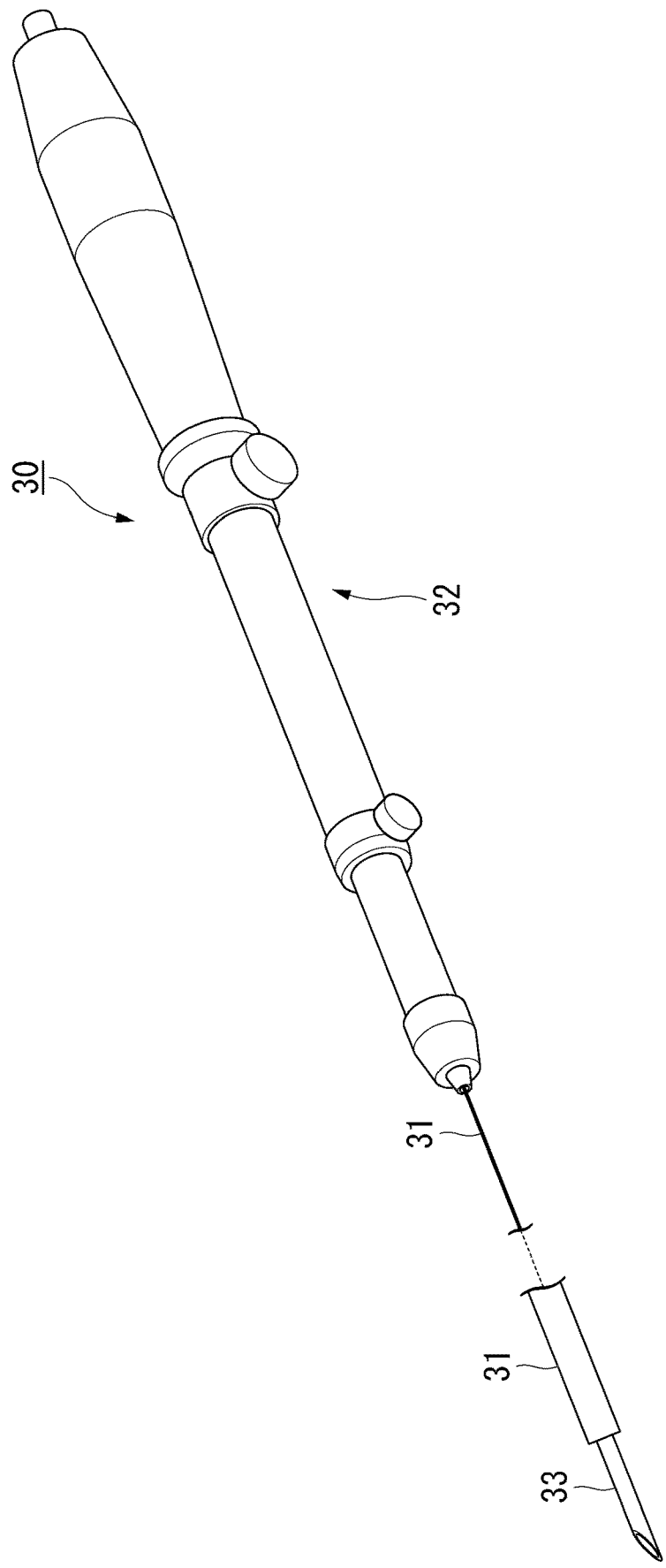
FIG. 5 is a diagram showing an example of a puncture device used in the access route-forming method of the present invention.

FIG. 5 shows an example of the puncture device. A puncture device 30 shown in FIG. 5 includes an elongated sheath 31, an operation part 32 attached to the sheath 31, and a needle tube 33 connected to the operation part 32. The needle tube 33 is passed through the sheath 31, and by operating the operation part 32, the needle tube 33 can be protruded from the sheath 31 or stored in the sheath 31.

The needle tube 33 may have one or more dimples having a recessed outer surface at the distal end. In this case, the ultrasound waves are easily reflected, and the position of the needle can be easily confirmed on the ultrasound image.

When the puncture device 30 is inserted into the endoscopic channel, the operator positions the distal end of the sheath 31 near the exit of the treatment device channel. When the endoscope has the raising base, the raising base may be raised in advance and the distal end of the sheath 31 may be inserted until it reaches the raising base. When the sheath 31 reaches the vicinity of the raising base, the operation part 32 may be fixed to the entrance of the treatment device channel.

The operator operates the endoscope and the puncture device to position the distal end of the sheath 31 within the field of view of the optical observation part 10. In a case where the endoscope has the raising base, the raising base may be operated as needed. At this point, as in the example shown in FIG. 6, the distal end of the needle tube 33 introduced into the duodenum is still in the sheath 31, and an opening Po and an oral side projection Op of the duodenal papilla and the distal end of the sheath 31 are imaged in the field of view.

Figure 6:
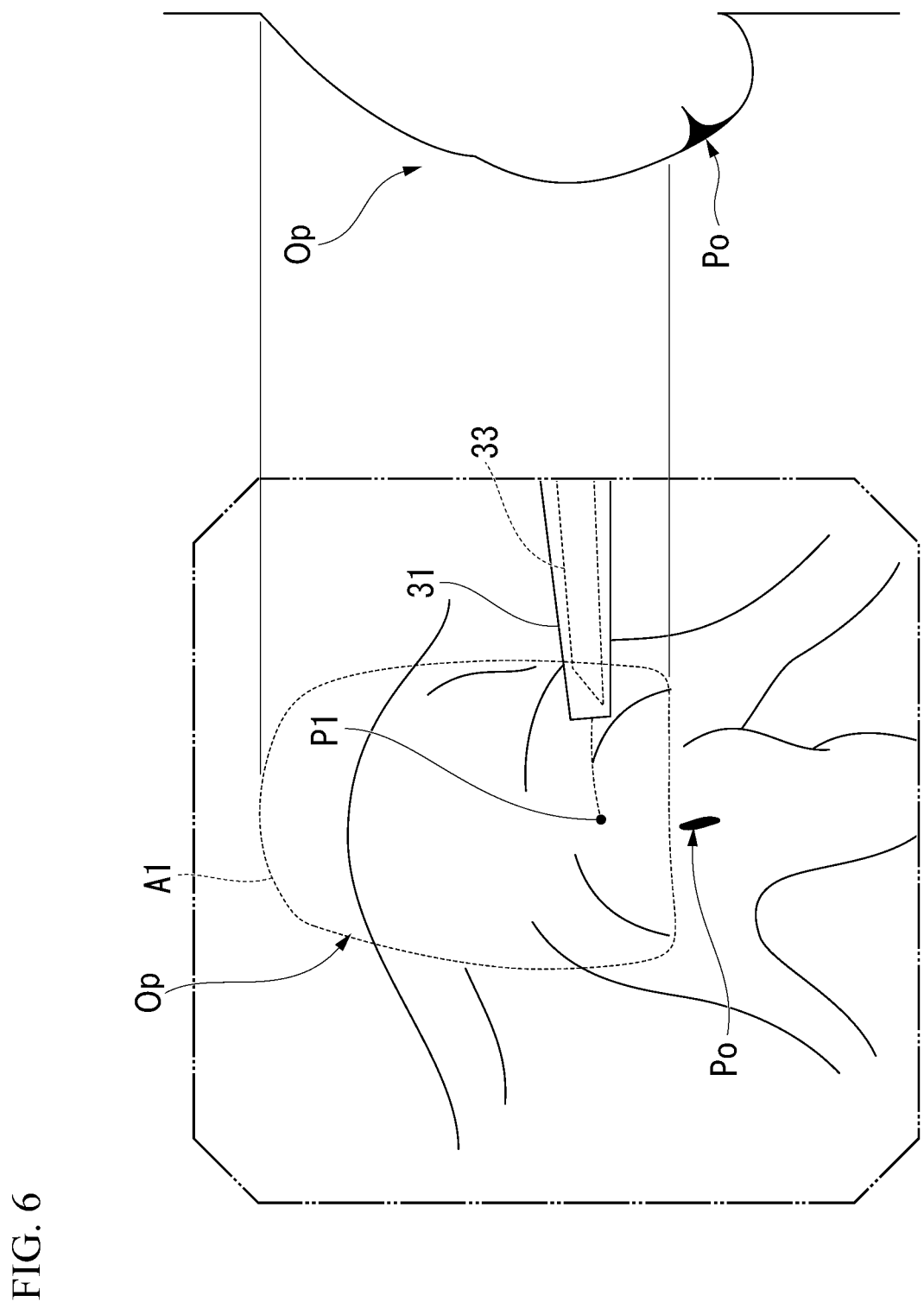
FIG. 6 is a diagram showing one process of an access route-forming method according to an embodiment.

The operator estimates a position P1 on the duodenal surface that coincides with the extension line of the sheath 31 while viewing the image as shown in FIG. 6 with an endoscope. That is, the position P1 means a position where it is presumed that the distal end of the sheath 31 and the inner surface of the duodenum come into contact with each other when the sheath 31 is advanced as it is.

The operator adjusts the position P1 by operating the endoscope so that the position P1 is within the range of the oral side projection Op and does not overlap with the opening Po. When the insertion portion of the endoscope is advanced or retracted, the insertion portion is bent in the vertical direction of the image, or the raising base is operated, the sheath 31 moves in the vertical direction in the image. When the insertion portion of the endoscope is twisted or the insertion portion is bent in the left-right direction of the image, the sheath 31 moves in the left-right direction in the image. By appropriately combining these operations, the position of the sheath 31 in the image can be changed and the position P1 can be adjusted.

After adjusting the position P1, the distal end of the sheath 31 may be brought into contact with the position P1. If the sheath 31 is brought into contact with the oral side projection on the oral side at this timing, there is an advantage in that the sheath position is less likely to shift when the sheath is aligned in the ultrasound image described later.

Since the opening Po is closed most of the time, it cannot be imaged by an ultrasound image. In addition, the resolution of the current ultrasound image is not sufficient enough for the oral side projection to be accurately imaged. Therefore, the above-mentioned aligning step in the optical image is required.

In FIG. 6, a preferable range of the position P1 is shown as an area A1. The area A1 is within the range of the oral side projection Op, which is a portion of the duodenal papilla raised from the inner wall of the duodenum on the oral side of the opening Po. The opening Po is not included in the oral side projection Op. If the position where the puncture device is punctured shifts to the left, right, up or down with respect to the area A1, the possibility of penetrating the duodenum and protruding into the abdominal cavity or stimulating the opening increases. By adjusting the position P1 within the area A1, the puncture device can be reliably punctured into the oral side projection and the risk described above can be reduced.

On the right side of FIG. 6, the cross-sectional shape of the oral side projection Op and its surroundings is schematically shown. In a case where the optical image has an assist function for displaying the protruding direction of the needle in the optical image, the position P1 can be adjusted in the area A1 by using this as a guide. In this case, the position P1 can be adjusted within the area A1 without having the distal end of the puncture device 30 protrude from the exit of the treatment device channel.

Next, while observing the ultrasound image by the ultrasound vibrator 13, moving the ultrasound vibrator 13, and changing the scanning surface from which the image is acquired, the operator selects the scanning surface in which the bile duct is imaged at the position closest to the duodenal papilla and holds the ultrasound vibrator 13.

During the procedure, both the optical image and the ultrasound image may be displayed at all times, or only one may be displayed while switching appropriately.

Figure 7:
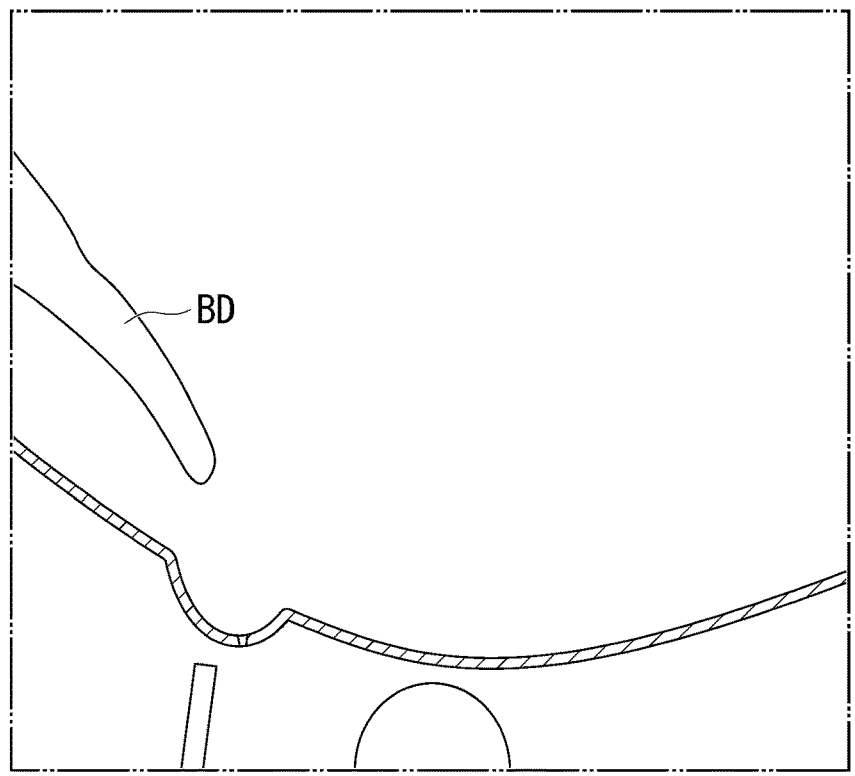
FIG. 7 is a diagram showing an example of an ultrasound image.
Figure 8:
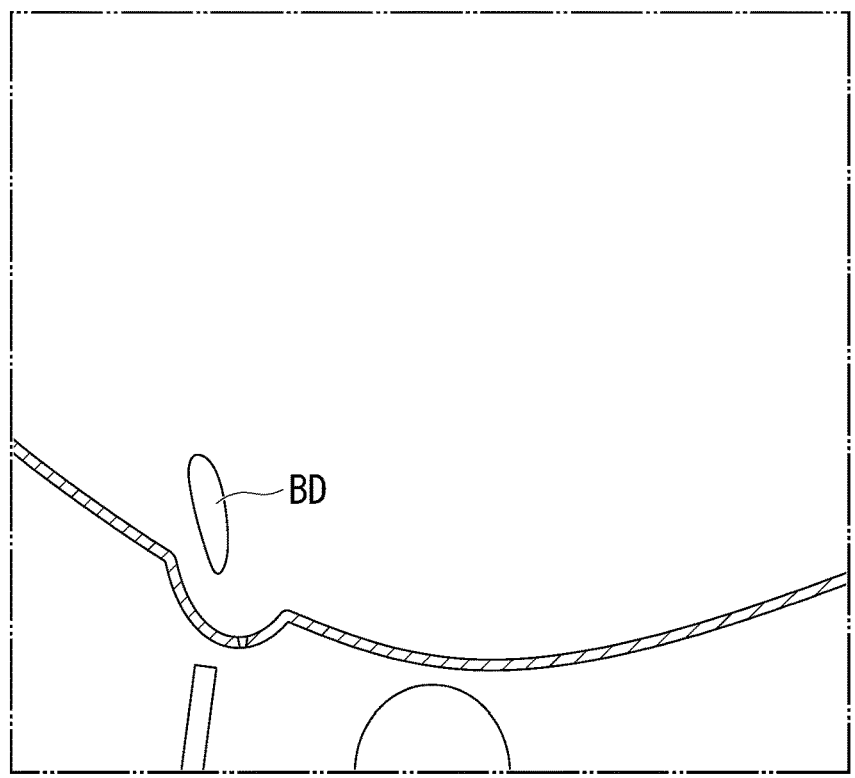
FIG. 8 is a diagram showing an example of an ultrasound image.

For example, in the ultrasound image shown in FIG. 7 and the ultrasound image shown in FIG. 8, compared with the bile duct BD imaged in FIG. 7, the lower bile duct BD closer to the duodenal papilla is imaged in FIG. 8. In such a case, the operator selects the scanning surface corresponding to FIG. 8.

As described above, the oral side projection is usually not accurately imaged in the ultrasound image, but in the drawings of the present specification, the oral side projection is shown in order to make it easier to understand the positional relationship with the bile duct.

The scanning surface is changed by operating the endoscope while taking care that the position P1 (the distal end of the sheath when the sheath 31 is in contact with the oral side projection) does not deviate from the area A1, and changing the emission direction of the ultrasound waves. Specifically, the scanning surface is adjusted by appropriately combining the advance/retract and the twist (rotation) of the endoscope, and the bending of the curved portion of the endoscupe in the vertical/horizontal directions.

The common duct after the bile duct and pancreatic duct merge is difficult to recognize on ultrasound images because the sphincter muscle of the duodenal papilla is narrowed or closed due to contraction most of the time. However, since the bile duct slightly above the upstream side of the confluence of the bile duct and the pancreatic duct remains open, it can be visually recognized by an ultrasound image. Although the bile duct has a complex three-dimensional shape, the lowermost part on the ultrasound image, which is the closest to the duodenal papilla, can be identified by the above steps.

Figure 9:
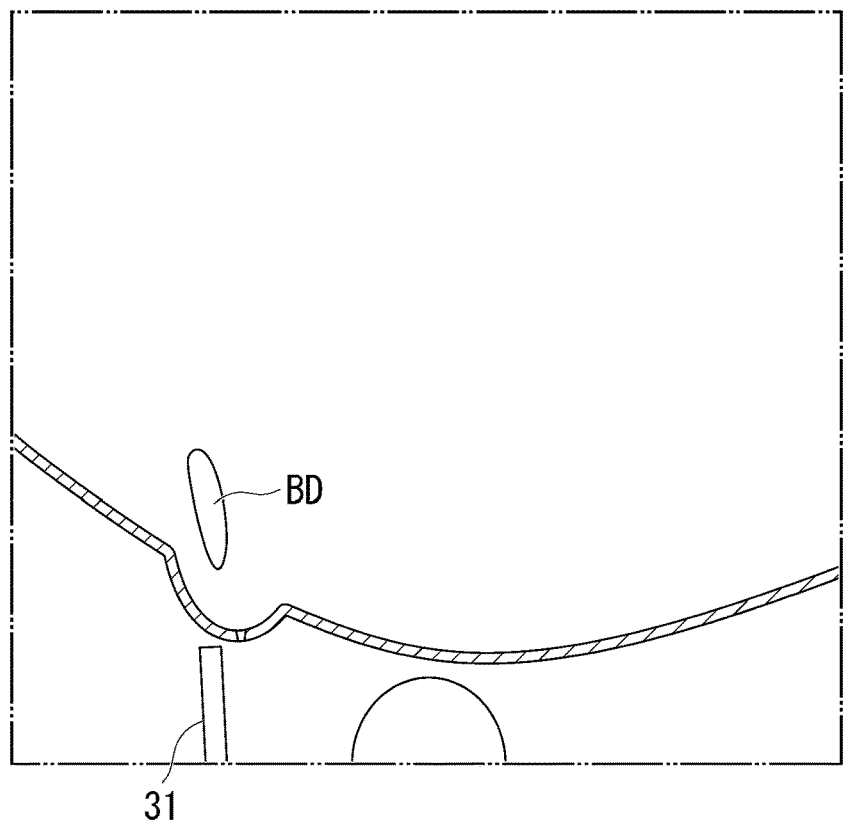
FIG. 9 is a diagram showing one process of the access route-forming method according to an embodiment.

The operator operates the sheath 31 while observing the ultrasound image, maintaining the position of the scanning surface so that the position P1 (the distal end of the sheath when the sheath 31 is in contact with the oral side projection) does not deviate from the area A1 and the lowermost part of the bile duct can be imaged, and positions the lowermost part of the bile duct BD on the extension line of the sheath 31 as shown in FIG. 9. Specifically, it is adjusted by appropriately combining the minute advance/retract and twist (rotation) of the endoscope, bending of the curved portion of the endoscope in the vertical and horizontal directions, and raising the raising base in a state where there is a raising base. Since water is stored in the duodenum, the sheath 31 is in a state where it can be imaged on an ultrasound image. Similarly, in a state where the ultrasound image has an assist function for displaying the needle protruding direction, the angle of the sheath with respect to the tissue may be adjusted so that the lowermost portion of the bile duct BD is positioned on the display of the needle protruding direction. At this time, the angle formed by the longitudinal axis of the sheath 31 and the extending direction of the bile duct BD on the downstream side of the bile duct is preferably as small as possible. As the angle becomes smaller, the longitudinal axis of the sheath 31 and the extending direction of the bile duct become closer to parallel.

The operator confirms on the ultrasound image that there is no pancreatic duct between the distal end of the sheath and the lowermost part of the bile duct on its extension line. In addition, the operator puts the endoscope in Doppler mode and confirms on ultrasound images that there are no blood vessels between the distal end of the sheath and the lowermost part of the bile duct. In a case where there are blood vessels, a predetermined color such as red or blue indicating blood flow is displayed on the ultrasound image.

In a case where there is either a pancreatic duct or a blood vessel between the distal end of the sheath and the lowermost part of the bile duct, if the needle tube is protruded as it is, there is a high possibility that the needle tube will pierce the pancreatic duct or blood vessel, so the position P1 is changed under optical observation, and the above procedure is performed again.

Either the presence or absence of the pancreatic duct or the presence or absence of the blood vessel may be confirmed first.

Figure 10:
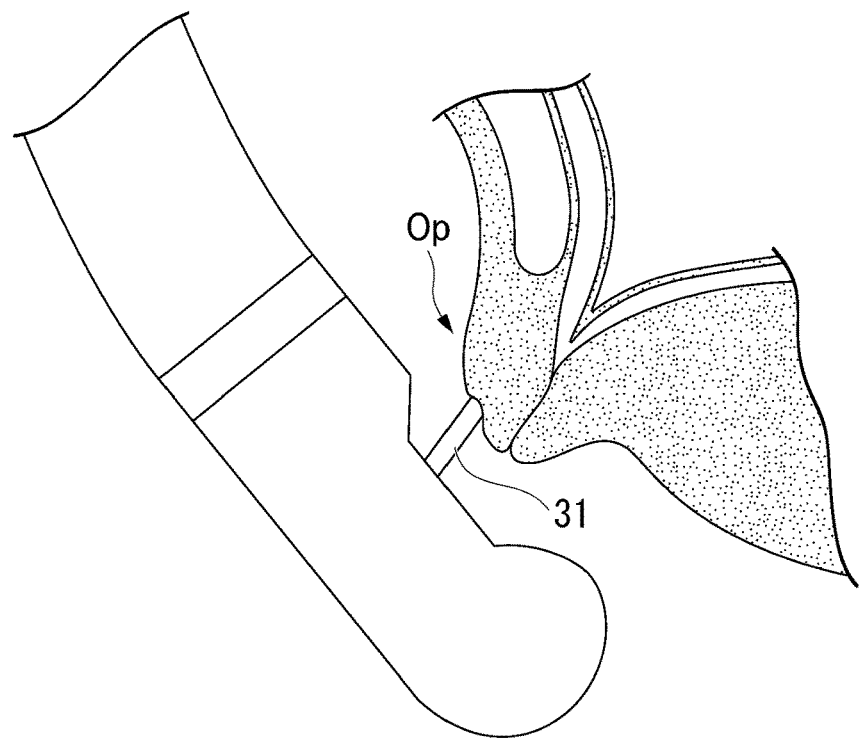
FIG. 10 is a diagram showing one process of the access route-forming method according to an embodiment.

By the above process, the piercing angle of the needle tube into the oral side projection, that is, the path for advancing the needle tube 33 within the tissue of the oral side projection is determined. The operator may advance the sheath 31 while maintaining the position and orientation of the endoscope under optical observation, bring the distal end of the sheath 31 close to the oral side projection, and lightly contact the sheath 31 as shown in FIG. 10. By this operation, the distal end of the sheath 31 comes into contact with the oral side projection Op approximately at the position P1 or in the vicinity of the position P1.

As described above, when the distal end of the sheath 31 is brought into contact with the position P1 before positioning in the ultrasound image, this operation is not necessary.

Figure 11:
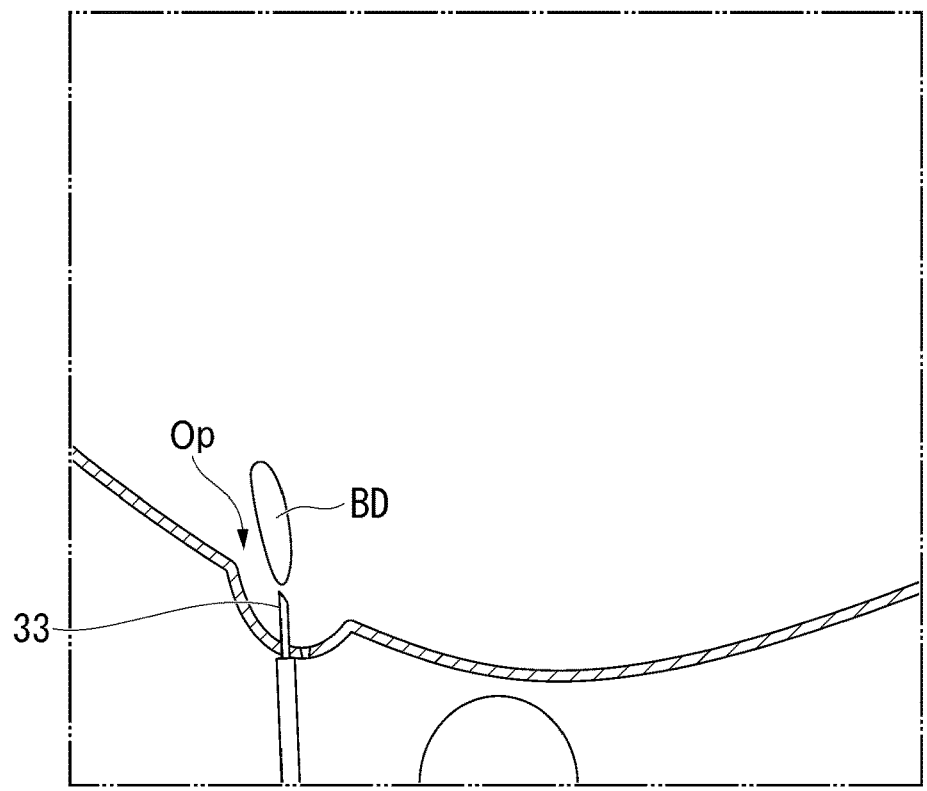
FIG. 11 is a diagram showing one process of the access route-forming method according to an embodiment.

Subsequently, the operator operates the operation part 32 of the puncture device 30 under ultrasound observation to protrude the needle tube 33 from the sheath 31. As shown in FIG. 11, the protruding needle tube 33 pierces the oral side projection Op. When the needle tube 33 is further advanced, the needle tube 33 advances in the tissue of the oral side projection Op toward the upstream side of the bile duct BD, and approaches the lowermost part of the bile duct BD without exiting the abdominal cavity. When the needle tube 33 pierces the bile duct BD and the distal end of the needle tube 33 reaches the inside of the bile duct BD, the operator stops the advance of the needle tube 33 and fixes it so as not to move with respect to the sheath 31.

If necessary, it may be confirmed by a method other than the ultrasound image whether or not the distal end of the needle tube 33 is in the bile duct. In particular, an exemplary example of the method is as follows:
  inject a contrast medium through the needle tube 33 and perform X-ray fluoroscopy;
  insert a guide member (described later) into the needle tube 33 and protrude it from the needle tube 33 to check its behavior, or
  suction from the needle tube 33 and check if bile is suctioned.

The needle tube 33 inserted into the oral side projection reaches the bile duct without exiting the abdominal cavity and without contacting any of the openings of the duodenal papilla, the pancreatic duct ostium, the common duct, the pancreatic duct, and large blood vessels. That is, the tunnel formed in the duodenum by the needle tube 33 is a tunnel that connects the inside of the duodenum and the bile duct without going out to the abdominal cavity and stimulating each of the above-mentioned sites. Since the needle tube 33 is stuck in the bile duct from the downstream side to the upstream side of the bile duct, it advances toward the upstream side when further advanced.

Figure 12:
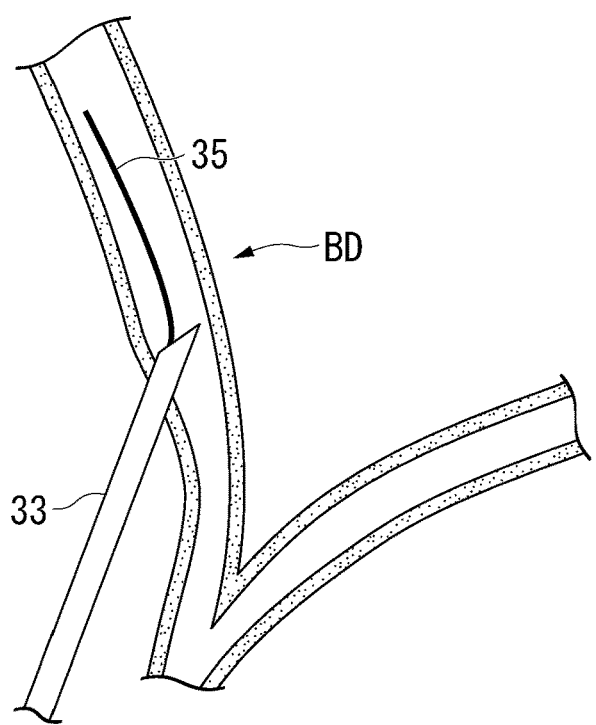
FIG. 12 is a diagram showing one process of the access route-forming method according to an embodiment.

The operator inserts a guide member (treatment device) 35 into the needle tube 33 from a proximal end of the puncture device 30, advances the guide member 35 inside the needle tube, and protrudes the guide member 35 from the distal end of the needle tube 33. A guide wire is typical as the guide member in the present embodiment. As shown in FIG. 12, the guide member 35 extends in the bile duct BD from the downstream side to the upstream side. The guide member 35 may have at least a distal end that is reflected in an X-ray image or an ultrasound image.

When the guide member 35 is sufficiently placed in the bile duct BD, the operator removes the puncture device 30 leaving the guide member 35. This forms an access route from the duodenum to the bile duct. This access route does not irritate these sites because it does not touch the opening of the duodenal papilla, the pancreatic duct ostium, or the common duct.

Figure 18:
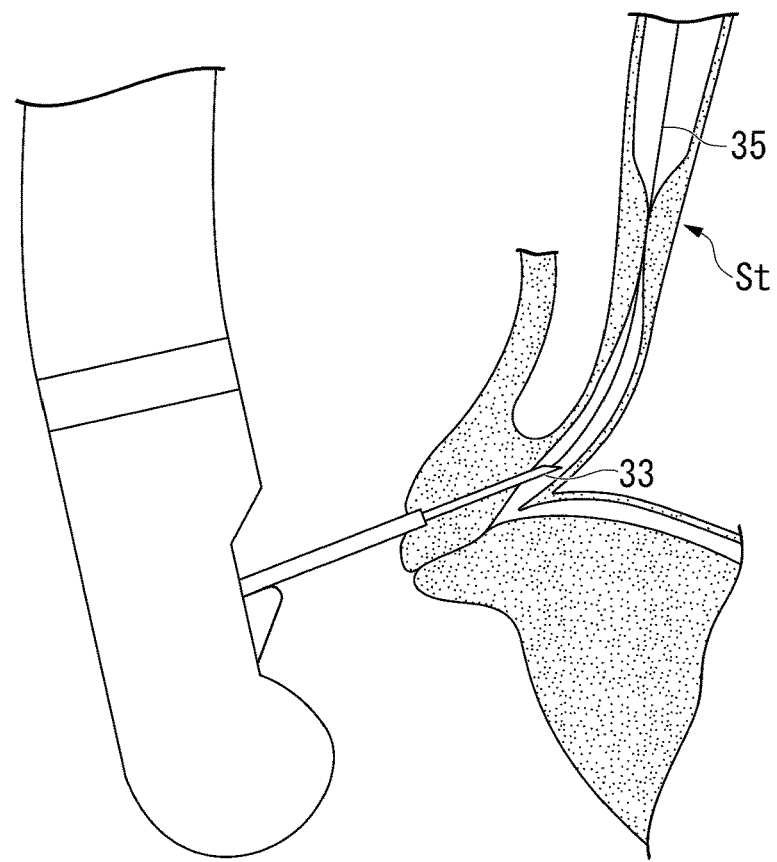
FIG. 18 is a diagram showing a state in which a guide member breaks through a stenosis.

If the stenosis of the bile duct is located near the oral ridge, it may be difficult to break through the stenosis even if only the guide member is advanced. In such a case, as shown in FIG. 18, by protruding the distal end of the needle tube 33 into the bile duct BD and then bringing the distal end of the needle tube 33 close to the stenosis St, it becomes easier to make the guide member 35 break through the stenosis.

Figure 19:
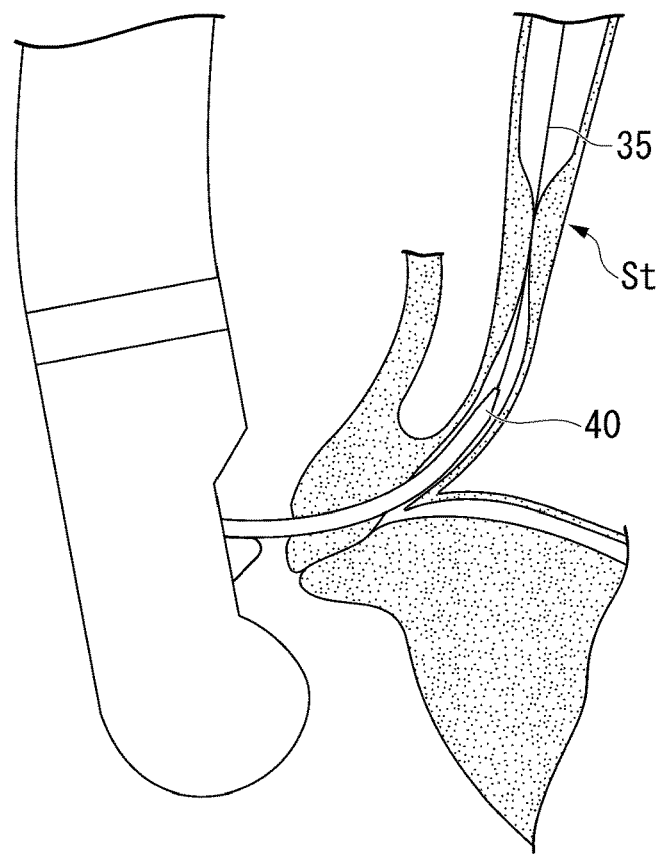
FIG. 19 is a diagram showing another example of a state in which the guide member breaks through the stenosis.

Alternatively, after removing the puncture device 30, a resin catheter may be inserted into the bile duct along the guide member 35, and as shown in FIG. 19, after the distal end of the catheter 40 is brought close to the stenosis St, the guide member 35 may be advanced. Since the catheter 40 is more flexible than the needle tube 33, it can be easily moved closer to the stenosis St than the needle tube 33, and the bile duct is less likely to be damaged even if it comes into contact with the bile duct wall. Further, since the resistance when advancing and retracting the guide member 35 in the catheter 40 is smaller than the resistance when advancing and retracting the guide member 35 in the needle tube 33, it is easy to transmit the force to the guide member 35 and it is easy to break through the stenosis St.

When using the catheter 40, it is necessary to be aware that the guide member may come off the bile duct when the puncture device 30 is replaced with the catheter 40.

Figure 20:
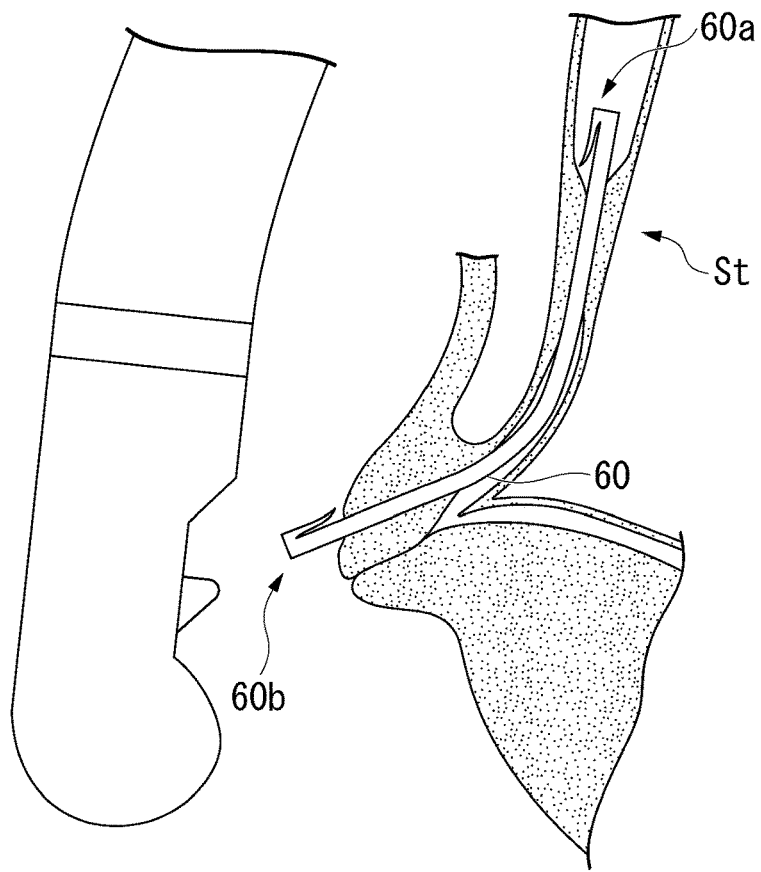
FIG. 20 is a diagram showing a state in which a drainage stent is placed in the bile duct.

After forming the access route, various treatments can be performed by introducing the distal ends of various treatment devices into the bile duct via the access route along the guide member 35. Some of them are shown below.
  A contrast catheter is inserted into the bile duct along the guide member 35, and ERCP is performed.
  A basket-type treatment device is inserted into the bile duct along the guide member 35 to treat intrabile duct calculus.
  A treatment device having a balloon is inserted into the bile duct along the guide member 35 to treat intrabile duct calculus and dilate a stenosis of the bile duct.
  A biopsy forceps is inserted into the bile duct along the guide member 35, and tissues such as the bile duct used for definitive diagnosis of malignant tumors and the like are collected.
  A stent delivery system is inserted into the bile duct along the guide member 35, and the stent (drainage stent) is placed in the bile duct. An example of placing the drainage stent is shown in FIG. 20. Normally, a first end portion 60a of a placed drainage stent 60 is located upstream of the stenosis St, and a second end portion 60b exits the tunnel and is located in the duodenum. That is, the stenosis St is located between the first end portion 60a and the second end portion 60b.

If there are a plurality of stenoses, a plurality of drainage stents can be placed. In addition to improving the flow of bile in the stenosis described above, the drainage stent can be placed for various purposes such as temporary biliary decompression before calculus removal, prevention of jaundice after calculus removal, and decompression in the bile duct during bile duct perforation. The drainage stent may be a tube stent or a metallic stent, and in the case of a metallic stent, it may be a covered metallic stent.

When performing the procedure, the access route may be dilated by performing endoscopic sphincterotomy (EST) or endoscopic papillary balloon dilatation (EPBD) as needed. Further, the access route may be extended by combining EST and EPBD.

As described above, according to the present embodiment, the route from within the duodenum to access the bile duct without touching the opening of the papilla of the duodenal papilla, the pancreatic duct ostium, and the common duct can be formed with significantly reduced risk of intestinal perforation and major bleeding. As a result, various treatments for the bile duct can be performed without stimulating the opening, the pancreatic duct ostium, and the common duct, and the occurrence of complications due to these stimuli can be significantly reduced. These advantages cannot be realized by the technique described in Published Japanese Translation No. 2013-507185 of the PCT International Publication, in which it is assumed that a stent is placed, the needle penetrates the duodenum and enters the abdominal cavity.

In addition, by combining optical observation with an endoscope and ultrasound observation, the path of the needle from the oral side projection to the bile duct can be easily identified without passing through a large blood vessel or pancreatic duct. Therefore, compared to the conventional ERCP, it does not require advanced skills and can be easily performed by many operators.

As another method for forming an access route from the oral side projection to the bile duct, a method of incising the oral side projection under optical observation is known. This method does not provide any information about the presence or absence of the abdominal cavity or the presence or absence of blood vessels or pancreatic ducts in the incised tissue. Therefore, the possibility of unintended perforation or bleeding cannot be reduced. A low-risk route from the oral side projection to the bile duct can be realized only by combining the determination of the insertion position under optical observation and the determination of the piercing angle under ultrasound observation as in the present embodiment.

In the access route-forming method of the present embodiment, the details of each process and the device used can be changed in various ways. Some of them will be described below.

(Curved Mode of the Endoscope Insertion Part)

Figure 13:
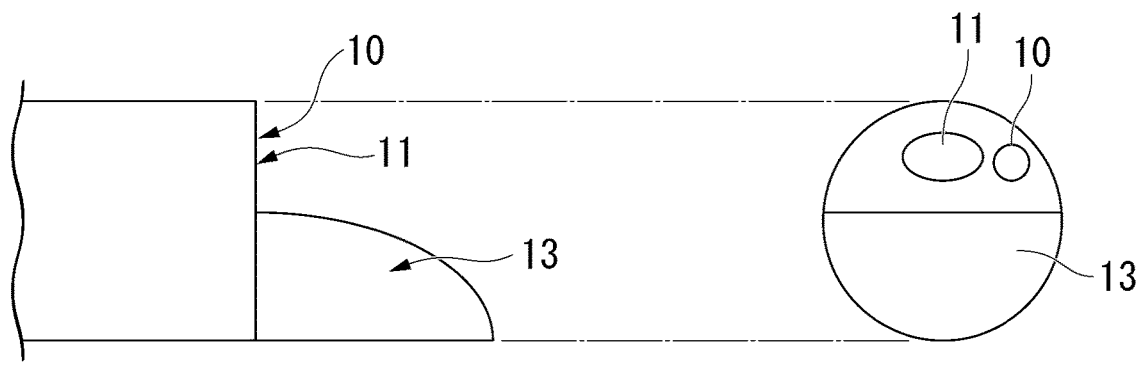
FIG. 13 is a diagram showing a distal end portion of an endoscope used in a modified mode.
Figure 14:
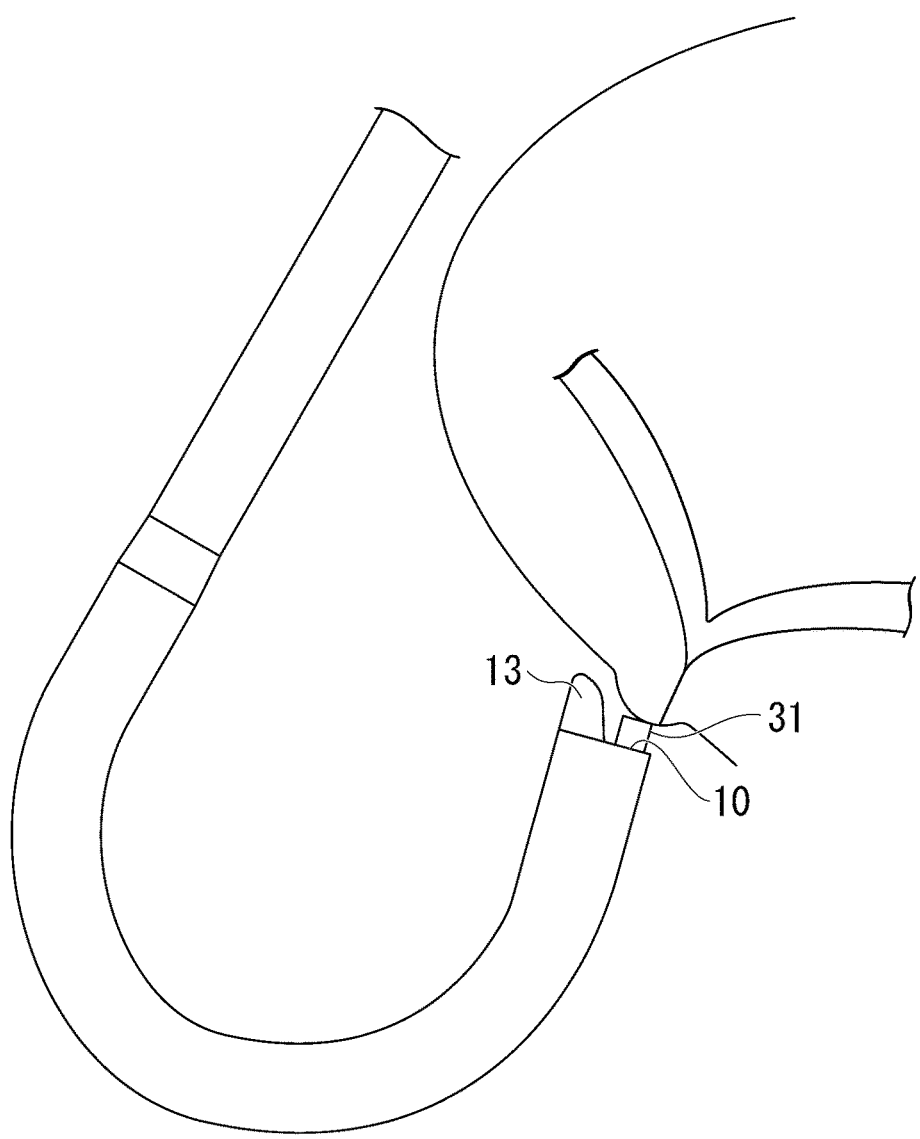
FIG. 14 is a diagram showing one process of an access route-forming method according to the modified mode.

In the above description, as shown in FIG. 4 and the like, the side-view type endoscope is curved so that the side where the optical observation part 10 is located is inside the curve. This embodiment has an advantage in that the orientation of the endoscope can be easily stabilized in the duodenum and optical observation as shown in FIG. 6 can be easily performed. As another embodiment, when a direct-view type endoscope in which the optical observation part 10 is provided at the distal end portion is used as shown in FIG. 13, the endoscope may be curved in one direction by about 180° and inverted as shown in FIG. 14. At this time, the endoscope may be curved so that the side with the optical observation part 10 is on the outside of the curve, or the side with the optical observation part 10 may be curved on the inside of the curve. In this case, the sheath 31 of the puncture device protruding from the outlet 11 can be inserted into the oral side projection without being strongly bent by a raising base or the like. As a result, the resistance when moving the sheath or needle tube of the puncture device back and forth is reduced, and the operation of the puncture device becomes smooth.

(Sheath Approach to the Oral Side Projection)

When the distal end of the sheath brought close to the oral side projection is brought into contact with the oral side projection, the sheath in contact with the oral side projection may be further pushed in, and the distal end of the sheath may be sunk into the oral side projection. In this case, since there is a tissue of the oral side projection around the distal end of the sheath, by bringing the ultrasound vibrator into contact with the duodenum wall, the distal end of the sheath can be imaged in an ultrasound image without storing water in the duodenum. As a result, it becomes possible to execute the access route-forming method by omitting the step of storing water.

(Device Configuration)

In the above description, a hollow needle tube was used as the needle to pierce the oral side projection.

Figure 15:
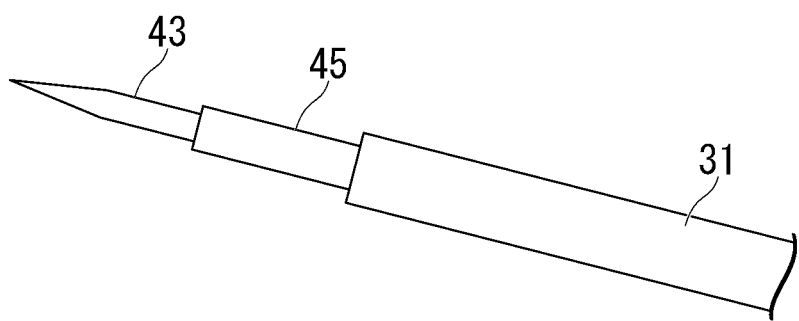
FIG. 15 is a diagram showing another example of the puncture device.

As another embodiment, a non-tubular solid needle 43 as shown in FIG. 15 may be used. In this case, as the guide member, a guide tube 45 having an inner diameter larger than the outer diameter of the needle 43 and an outer diameter smaller than the inner diameter of the sheath 31 can be used. The outer diameter of the guide tube 45 is small enough to pass through the guide wire lumen of the treatment device to be introduced later.

In the above description, an endoscope in which an ultrasound vibrator is attached to the insertion portion is used. As another embodiment, an ultrasound probe (hereinafter referred to as "insertion probe") equipped with an ultrasound vibrator having a size that can be passed through the treatment device channel of the endoscope may be combined with an endoscope capable of only optical observation, to execute the access route formation method.

In this case, a duodenal endoscope is inserted into the luminal organ through the patient's mouth or nose, and the distal end is moved to the vicinity of the duodenal papilla. Next, the duodenal papilla is imaged in the field of view of the optical observation part of the duodenal endoscope. When imaging the duodenal papilla in the field of view, it is desirable to position the duodenal papilla in front (center) of the optical image.

Next, the operator inserts the insertion probe into the treatment device channel from the entrance of the treatment device channel provided in the operation part of the endoscope.

When inserting the insertion probe into the endoscopic channel, the operator positions the distal end of the insertion probe near the exit of the treatment instrument channel. When the endoscope has the raising base, the raising base may be kept upright when the insertion probe is inserted, and the insertion probe may be inserted until the distal end of the insertion probe reaches the raising base. Further, when the distal end of the insertion probe reaches the vicinity of the raising base, the operation portion of the insertion probe may be attached to the entrance of the treatment device channel and fixed.

The operator then operates the endoscope and the insertion probe to position the distal end of the insertion probe within the field of view of the optical observation part.

Figure 16:
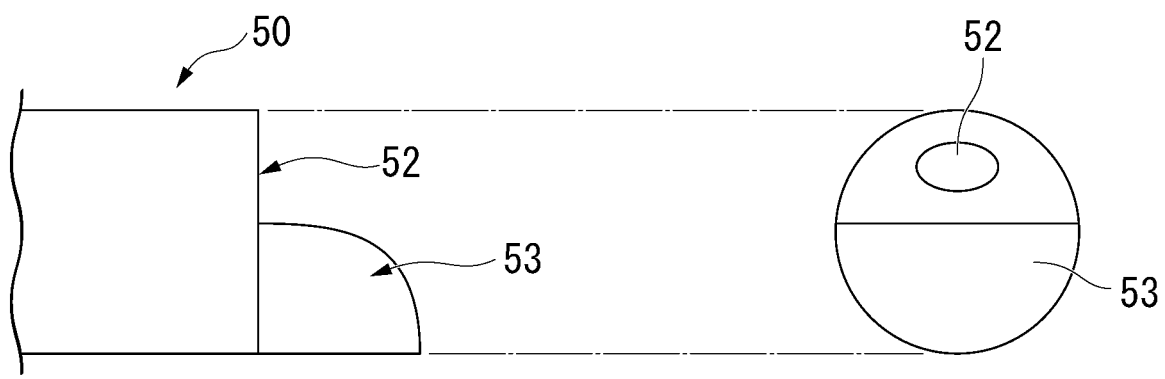
FIG. 16 is a diagram showing a distal end portion of an insertion probe according to the modified mode.

FIG. 16 shows the distal end of an insertion probe 50. The insertion probe 50 has a structure in which an ultrasound vibrator 53 is attached to the distal end of an elongated insertion portion. A channel extends in the longitudinal direction at the insertion portion, and an outlet 52 opens at the distal end.

The operator adjusts the position P1 by operating the endoscope so that the position P1 is within the range of the oral side projection Op and does not overlap with the opening Po. The position P1 at this time is a position on the surface of the duodenum that coincides with the extension line of the longitudinal axis of the insertion probe 50. When the insertion portion of the endoscope is advanced or retracted, the insertion portion is curved in the vertical direction of the image, or the raising base is operated, and the distal end of the insertion probe 50 moves in the vertical direction in the image. When the insertion portion of the endoscope is twisted or the insertion portion is curved in the left-right direction of the image, the distal end of the insertion probe 50 moves in the left-right direction in the image. By appropriately combining these operations, the position of the distal end of the insertion probe in the image can be changed and the position P1 can be adjusted.

After adjusting the position P1, the ultrasound vibrator 53 at the distal end of the insertion probe 50 is lightly brought into contact with the oral side projection Op.

The insertion probe 50 has an assist function of displaying the protruding direction of the needle on the ultrasound image. The operator confirms the bile duct and the pancreatic duct with the ultrasound image acquired by the insertion probe 50, and identifies the bile duct from the difference in direction (running).

Next, the operator moves the ultrasound vibrator 53 while viewing the ultrasound image by the ultrasound vibrator 53 to change the scanning surface from which the image is acquired in various ways, and selects the scanning surface in which the bile duct is imaged closest to the duodenal papilla and holds the ultrasound vibrator 53. Specifically, the scanning surface is adjusted by appropriately combining the advance/retract or the twist (rotation) of the endoscope, the bending of the curved portion of the endoscope in the vertical/horizontal directions, and the operation of the raising base.

In addition, the display of the assist function is adjusted to pass through the lowermost part of the bile duct. The specific operation is almost the same as the adjustment of the scanning surface described above.

Further, as in the above-described embodiment, the following is performed.

Check that there are no blood vessels on the assist display in Doppler mode for ultrasound observation. (This step can be omitted.)

Check that there is no pancreatic duct on the assist display on the ultrasound image. Either the confirmation that there is no blood vessel or the confirmation that there is no pancreatic duct may be performed first.

Up to this point, the insertion route of the needle tube 33 is determined.

Figure 17:
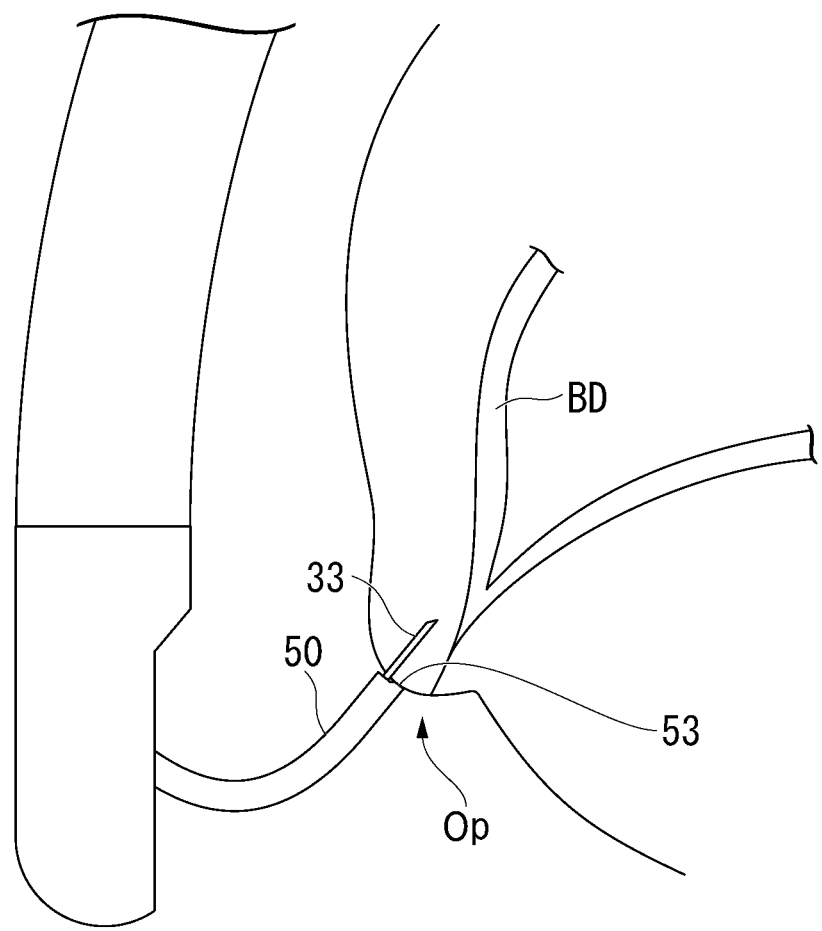
FIG. 17 is a diagram showing one process of the access mute-forming method according to the modified mode.

After determining the insertion route, the needle tube 33 is inserted into the oral side projection Op from the insertion probe 50 as shown in FIG. 17. Check the distal end of the needle on the ultrasound image, and stop the needle when the distal end of the needle reaches the inside of the bile duct BD.

The insertion portion of the insertion probe 50 may be provided with a mechanism capable of bending in advance or actively bending. In this way, as shown in FIG. 17, the insertion probe 50 protruding from the endoscope can be easily directed to retract towards the proximal end of the endoscope.

if necessary, confirm whether the distal end of the needle has reached the inside of the bile duct by means other than the ultrasound waves described above. (This step can be omitted.)

Insert the guide member deep into the bile duct while checking it with an X-ray image or an ultrasound image. (At least the distal end of which is reflected in the X-ray image or ultrasound image is used as the guide member)

Remove the insertion probe 50 from the bile duct and scope, leaving the guide member.

Use the guide member as a guide to perform ERCP or the related procedure described above.

In this embodiment using the insertion probe 50, the ultrasound vibrator 53 is brought into contact with the oral side projection Op, and the above-mentioned assist function can be used, so that the step of storing water in the duodenum can be omitted. As a result, the procedure becomes simpler.

In this embodiment, the needle tube 33 may be attached to and integrated with the insertion probe 50.

The second embodiment of the present invention will be described with reference to FIGS. 21 to 26. In the following description, duplicate description may be omitted for the contents already described.

In the present embodiment, the tunnel formed by piercing the ridge on the oral side with a needle is dilated larger than at the time of formation, making it easier to perform various subsequent procedures.

There are three main means of dilation: energizing dilator, catheter, and knife.

When using an energizing dilator, the lumen of a tunnel Tn can be dilated by inserting the dilator along the guide member 35 while energizing the tunnel Tn.

Figure 22:
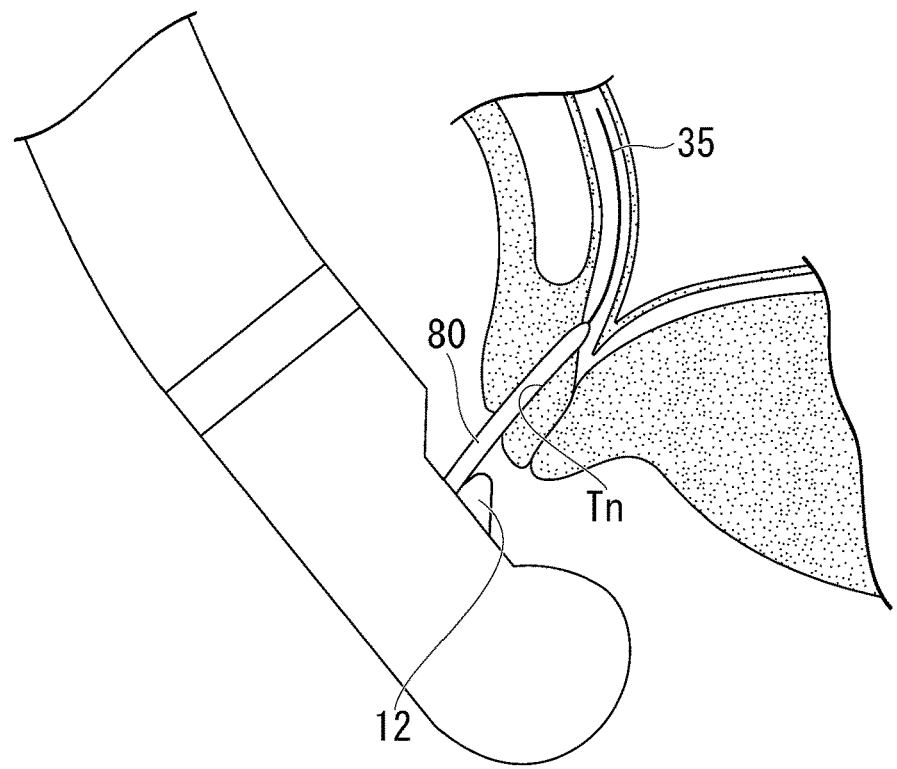
FIG. 22 is a diagram showing one process of the access route-forming method according to the second embodiment.

When a catheter is used, the lumen of the tunnel Tn can be dilated by inserting the catheter into the tunnel Tn along the guide member 35 and positioning a catheter 80 in the tunnel Tn for a certain period of time as shown in FIG. 22.

As the catheter to be used, those in which the diameter of the distal end portion is gradually reduced as it approaches the distal end, those in which the values of the inner diameter and outer diameter of the distal end are close to the values of the outer diameter of the guide member (for example, the difference between the outer diameter of the guide member and the outer diameter of the distal end of the catheter is about 0.8 mm), and those with moderate hardness and excellent pushability are preferable.

Some catheters include an X-ray opaque marker, and some catheters include a contrast medium that is kneaded. When such a catheter is used, the position of the catheter can be easily confirmed by an X-ray image or the like, and the catheter can be reliably arranged in the entire tunnel Tn. In addition, it is possible to determine that the catheter is pushed into the bile duct, and it is possible to determine that the entire tunnel Tn is reliably dilated.

Since the tunnel Tn formed by the needle is thin, it may be difficult for the catheter 80 to enter. In this case, the following operations are effective. Two or more of these operations may be combined.

Making the exit of the treatment tool channel approach the oral ridge by bending the bending mechanism of the endoscope.

Adding a push by the raising base 12 by lowering the raising base 12 once and then raising the raising base 12 in accordance with the operation of pushing the catheter 80.

Pushing the catheter 80 while rotating it.

If it is difficult to enter the tunnel Tn due to insufficient pushability of the catheter, a catheter equipped with an energizing tip at the distal end may be used. Since this catheter (energizing dilator) can cauterize and incise the tissue by bringing the energizing tip into contact with the tissue, the opening of the tunnel Tn can be widened for easy insertion. By advancing while energizing in the tunnel Tn, in addition to the dilation by the catheter, the dilation by incising the inner wall of the tunnel Tn can also be performed.

When using a knife, the knife is inserted into the tunnel Tn along the guide member 35, and the knife is energized while it is positioned in the tunnel Tn. The lumen of the tunnel Tn can be dilated by incising the inner wall of the tunnel Tn by energization.

Figure 23:
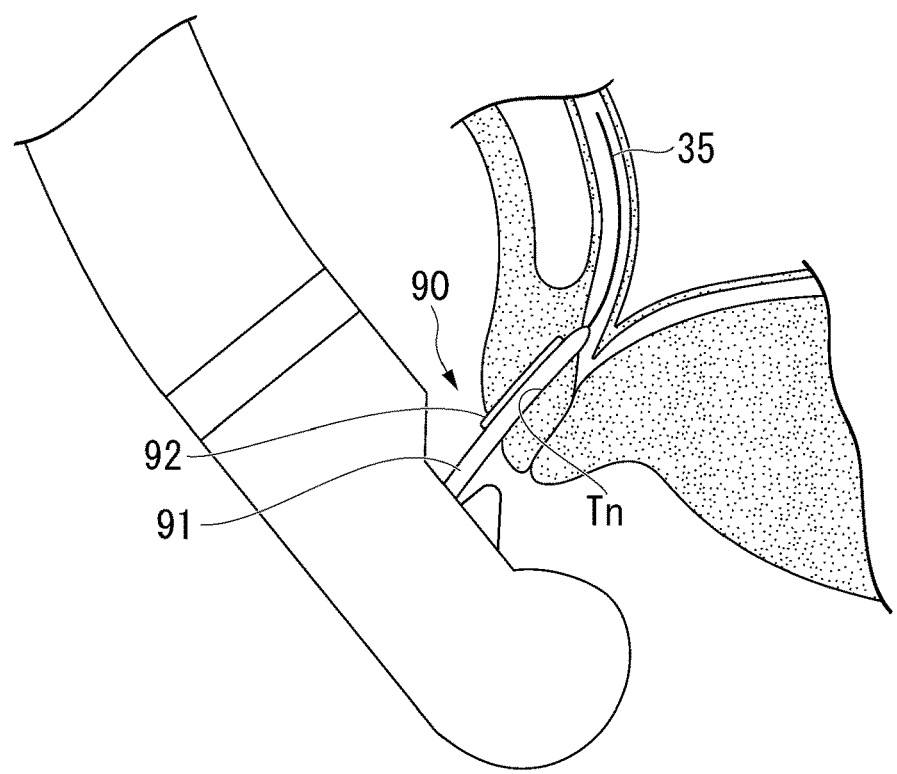
FIG. 23 is a diagram showing one process of the access route-forming method according to the second embodiment.

As the knife to be used, a sphincterotome used for the above-mentioned EST is suitable. FIG. 23 shows a state in which a sphincterotome 90 is positioned in the tunnel Tn. The sphincterotome 90 has a wire knife 92 arranged along the outer peripheral surface of the tube 91. When dilating the lumen of the tunnel Tn, first, the distal end of the tube 91 (including the wire knife 92) is inserted into the tunnel Tn, and the wire knife 92 is energized from the site in contact with the tissue to make an initial incision. At that time, the wire knife 92 may or may not be stretched in a bow shape. Then, while incising the tissue with a wire knife 92, the tube 91 is pushed deep into the tunnel Tn to extend the total length of the tunnel Tn. The present invention is not limited to this, and the sphincterotome 90 may be first inserted deep into the tunnel Tn, and then an energization incision may be made. Specifically, first, the distal end of the tube 91 is inserted as deep as possible in the tunnel Tn in a state where the knife wire 92 is aligned with the tube 91 as much as possible (a state in which the radius of curvature of the curve of the tube 91 is increased, and a state in which the wire knife 92 is not stretched in an arch shape). At that time, the distal end of the wire knife 92 is located in the deep part of the tunnel Tn or in the bile duct, and the proximal end of the wire knife 92 is located in the duodenum. After that, the wire knife 92 is energized to make an incision in the tissue.

For the incision with the sphincterotome, the operator may appropriately adjust the tension of the wire knife 92, the number of times of energization, the amount of incision, and the like according to the dilation amount of the tunnel Tn desired by the operator. The incision position is preferably on the mouth side of the inner wall of the tunnel Tn, and more preferably in the range of 11:00 to 12:00 when the front image of the mouth-side ridge Op shown in FIG. 6 is regarded as a clock face.

After dilating the lumen of the tunnel Tn, various treatments and observations described in the first embodiment can be performed. Due to the dilation of the tunnel Tn, various devices used for treatment can be easily inserted into the bile duct from the duodenum via the tunnel.

When placing a plurality of drainage stents, placing large-diameter drainage stents, removing large calculus, or the like, it is preferable to further dilate the tunnel Tn, and balloons and knives are suitable as means.

Figure 21:
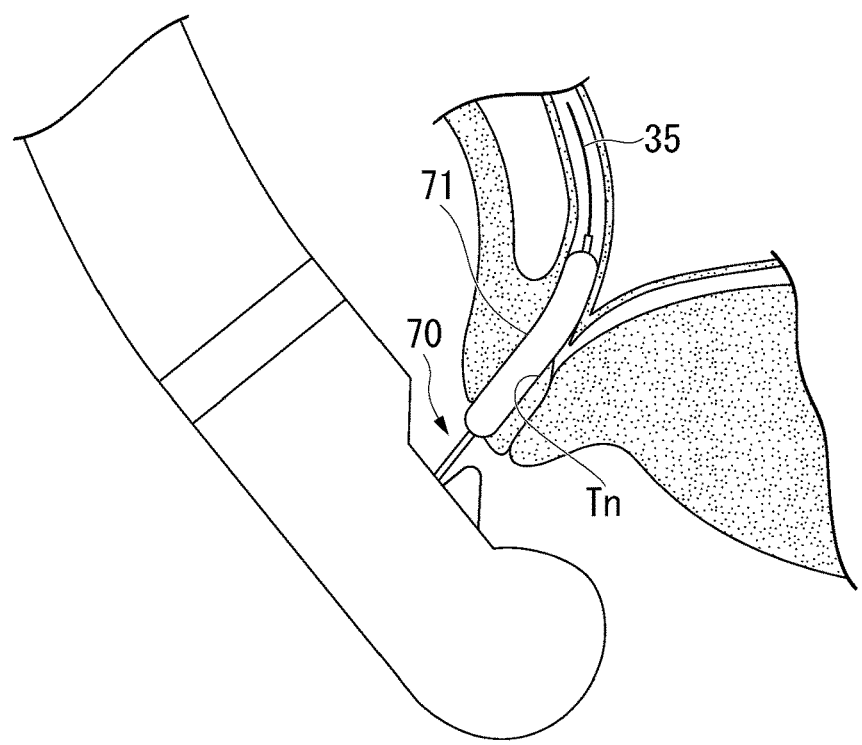
FIG. 21 is a diagram showing one process of an access route-forming method according to a second embodiment.

When desiring to greatly dilate the lumen of the tunnel Tn using a balloon, a balloon catheter 70 to which a balloon 71 is attached is inserted into the tunnel Tn formed along the guide member 35, and the balloon 71 is dilated in the tunnel in as shown in FIG. 21, so that the lumen of the tunnel Tn can be dilated. When dilating the tunnel Tn with the balloon 71, the distal end of the balloon 71 is located in the bile duct and the proximal end of the balloon 71 is located in the duodenum.

If the balloon catheter 70 does not enter the lumen of the tunnel Tn, the balloon catheter 70 may be inserted into the tunnel Tn after being slightly dilated in advance with the energizing dilator, catheter, knife, or the like, and then may be further dilated by the balloon as described above.

When desiring to greatly dilate the lumen of the tunnel Tn using a knife without using a balloon catheter or the like, as described above, by incising the tissue while appropriately adjusting the tension of the wire knife 92, the number of times of energization, the amount of incision, or the like, the lumen of the tunnel Tn may be dilated to the extent that a treatment tool such as a stent or a calculus can pass through.

Figure 24:
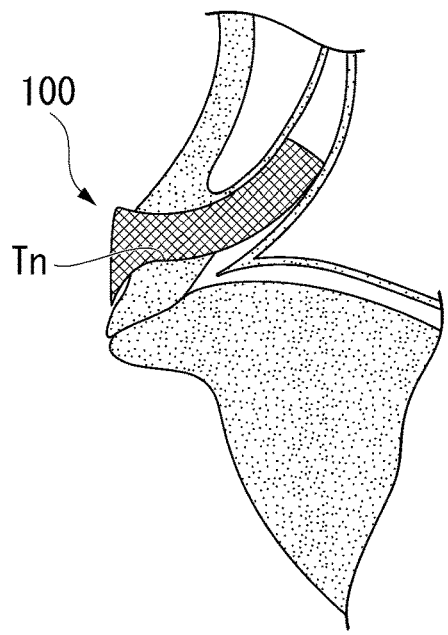
FIG. 24 is a diagram showing a state in which a stent is placed in a tunnel.

Since the dilated tunnel may gradually shrink thereafter, a stent 100 may be placed in the tunnel Tn as shown in FIG. 24. At that time, an end of the stent on the proximal side is located in the duodenum, and an end of the stent on the distal side is located in the bile duct (or in the tunnel). The stent 100 may be made of plastic, but it is preferable to use a self-dilatable metallic stent having a self-dilating ability, for example, a self-dilatable stent having a self-dilating ability formed by using a metal wire or the like because it is easier to maintain the dilated state. The self-dilatable stent may be a covered stent provided with a coating.

Figure 25:
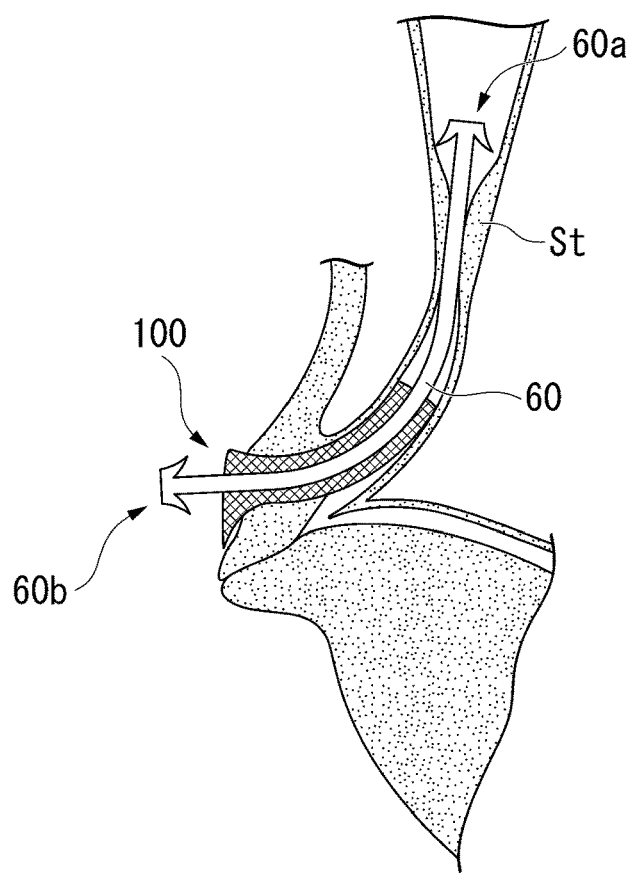
FIG. 25 is a diagram showing a state in which a drainage stent is placed in the bile duct while a stent is placed in the tunnel.

FIG. 25 shows an example of a state in which the drainage stent 60 is placed in the bile duct while the stent 100 is placed in the tunnel Tn. Both the stenosis St and the stent 100 are located between both end portions 60a and 60b of the drainage stent 60. Further, the present invention is not limited to this, and the proximal end of the drainage stent may be located in the bile duct.

Figure 26:
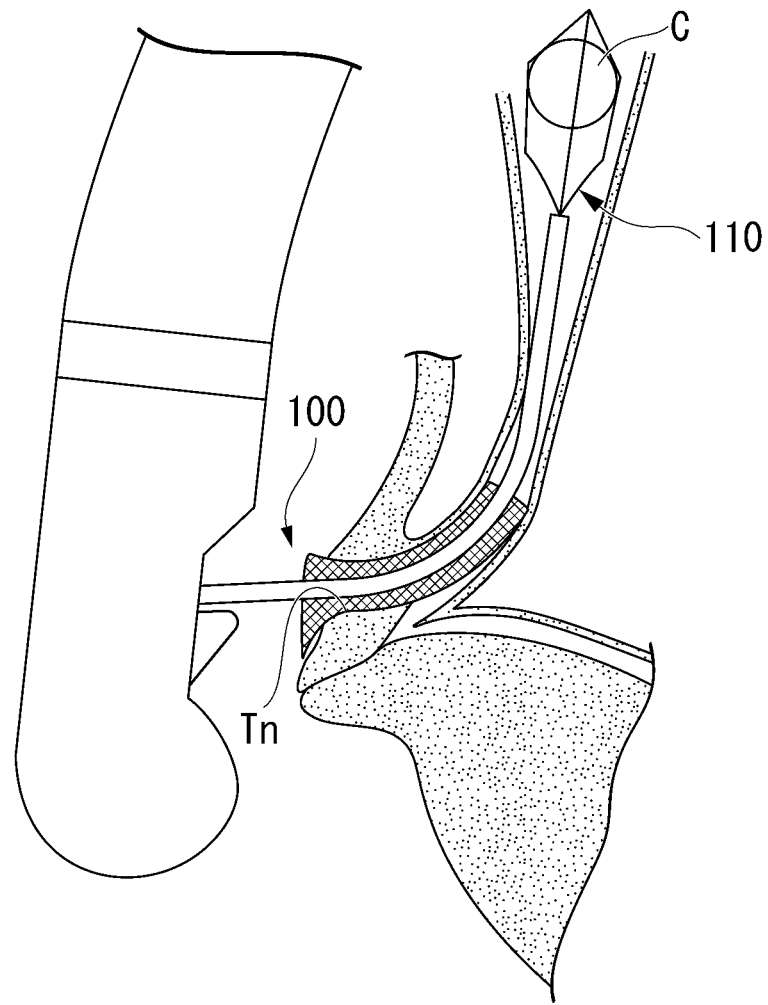
FIG. 26 is a diagram showing a state in which the stent is placed in a tunnel and calculus in the bile duct is removed.

FIG. 26 shows an example of a state in which calculus C is removed by a basket-type treatment tool 110 while the stent 100 is placed in the tunnel Tn. Since the tunnel Tn is dilated by the stent 100, even a large calculus can be taken out from the bile duct without being crushed. If the calculus is not very large, the calculus may be scraped out with a calculus balloon inflated upstream of the calculus, or if the calculus is too large to pass through the stent 100, the calculus may be crushed and then removed out of the bile duct.

While the stent 100 is placed in the tunnel Tn, a cholangioscope may be inserted into the bile duct through the stent 100 to perform diagnosis or treatment.

The stent 100 may be removed after the desired observation or treatment is completed.

Although the present invention has been described above using one embodiment and its modified mode, the technical scope of the present invention is not limited to the above-described embodiment. It is possible to change the combination of components, make various changes to each component, and delete them without departing from the spirit of the present invention.

Figure 27:
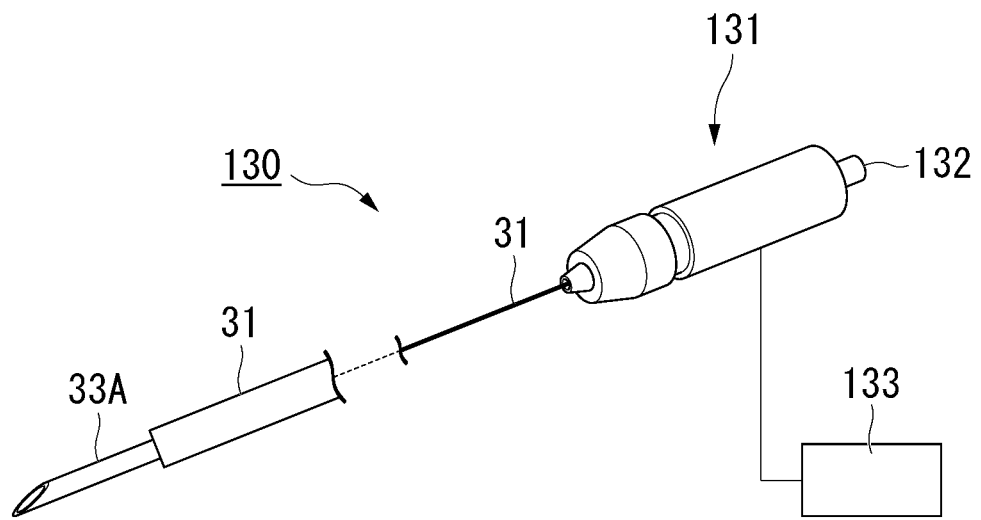
FIG. 27 is a schematic diagram of a puncture device provided with a needle tube having an energizing function.

For example, the needle used to form a tunnel may be configured to be energized. FIG. 27 shows a schematic view of a puncture device 130 including an energizable needle tube 33A. An operation part 131 attached to the sheath 31 has a guide wire port 132 and is connected to a power supply 133. When a current is supplied from the power supply 133 to the needle tube 33A in a state where the distal end of the metal needle tube 33A is in contact with the tissue, the tissue in contact with the distal end of the needle tube 33A is energized. The needle tube 33A does not need to extend over the entire length of the sheath 31, and for example, the needle tube 33A may be connected to the distal end of the resin tube extending from the operation part 131 to the middle of the sheath 31, and the power supply 133 and the metal needle tube 33A may be connected by a metal wire.

Since the needle tube used in the present invention needs to pass through an endoscope that is strongly curved toward the duodenal papilla, there is a limit to the pushability that can be imparted. Since the needle tube 33A can be inserted into the oral ridge while cauterizing the tissue by energization, it can be inserted into the tissue with a smaller force than the needle tube without the energization function. Therefore, the pushability required is lower than that of a needle tube having no energizing function, and the operability in the endoscope can be improved.

After forming the tunnel with the puncture device 130, the guide member 35 can be easily placed in the bile duct by inserting the guide member 35 into the guide wire port 132 and projecting it from the needle tube 33A in the same manner as described above.

The guide member 35 may be independently inserted into the bile duct from the tunnel after the needle tube 33A is removed from the tunnel.

The puncture device 130 may be configured to be fixed to the endoscope.

In addition to the puncture device 130, a catheter equipped with an energizing tip at the distal end described above can also be used for forming a tunnel.

A balloon covering the ultrasonic transducer may be attached to the endoscope so that the balloon can be filled with liquid. By doing so, the liquid-filled balloon is brought into contact with the duodenum wall, so that the distal end of the sheath can be visualized on an ultrasound image without storing water in the duodenum. In this case, it is sufficient that a part of the puncture device 130, for example, the distal end of the sheath is pressed against the oral ridge, or the puncture device 130 is recessed into the oral ridge.

What is claimed is:

1. A method for forming an access route to a bile duct, the method comprising:
    forming a tunnel extending from an oral ridge of a duodenal papilla, which is located on an oral side of a natural opening of the duodenal papilla, to the bile duct; and
    dilating a lumen of the tunnel more than when it was formed.

2. The method according to claim 1, wherein the tunnel is formed by piercing a needle from the oral ridge toward the bile duct.

3. The method according to claim 1, wherein the dilating of the lumen includes dilating by inflating a balloon.

4. The method according to claim 1, wherein the dilating of the lumen includes making an incision in an inner wall of the tunnel with a knife.

5. The method according to claim 1, wherein the dilating of the lumen includes placing a catheter within the tunnel.

6. The method according to claim 5, further comprising:
    after removing the catheter, inserting a treatment tool from a duodenum into the bile duct along a guide wire inserted in the dilated tunnel.

7. The method according to claim 1, further comprising:
    inserting a treatment tool into the dilated tunnel.

8. The method according to claim 2, further comprising:
    protruding a guide wire from the needle,
    wherein the needle is removed while leaving the guide wire.

9. The method according to claim 3, further comprising:
    after removing the balloon, inserting a treatment tool from inside a duodenum into the dilated tunnel.

10. The method according to claim 4, further comprising:
    after removing the knife, inserting a treatment tool from inside a duodenum into the dilated tunnel.

11. A method for forming an access route to a bile duct, the method comprising:
    forming a tunnel extending from an oral ridge of a duodenal papilla, which is located on an oral side of a natural opening of the duodenal papilla, to the bile duct; and
    placing a stent so that at least a part of the stent is located in the tunnel.

12. The method according to claim 11, wherein the tunnel is formed by piercing a needle from the oral ridge toward the bile duct.

13. The method according to claim 12, further comprising:
    protruding a guide wire from the needle,
    wherein the needle is removed while leaving the guide wire, and
    the stent is placed with the guide wire as a guide.

14. The method according to claim 11, wherein the stent has self-dilating ability, the method comprising:
    inserting a treatment tool into the stent.

15. The method according to claim 11, wherein the stent has self-dilating ability, the method comprising:
    inserting a drainage stent into the stent; and
    placing the drainage stent so that the stent and a stenotic site formed in the bile duct are located between both ends of the drainage stent.

16. A method for forming an access route to a bile duct, the method comprising:
    forming a tunnel extending from an oral ridge of a duodenal papilla, which is located on an oral side of a natural opening of the duodenal papilla, to the bile duct,
    wherein the tunnel is formed by piercing a needle, which is configured to energize a tissue, from the oral ridge toward the bile duct.

17. The method according to claim 16, further comprising:
    placing a drainage stent in the tunnel.

18. The method according to claim 16, further comprising:
    dilating a lumen of the tunnel by a balloon.

19. The method according to claim 16, further comprising:
    incising an inner wall of the tunnel with a knife.

20. The method according to claim 16, further comprising:
    placing a catheter in the tunnel.

* * * * *